(12) United States Patent
Woodburn et al.

(10) Patent No.: US 8,992,617 B2
(45) Date of Patent: Mar. 31, 2015

(54) ADJUSTABLE INTERVERTEBRAL IMPLANT

(75) Inventors: William Woodburn, Mantua, NJ (US); David Evans, Downingtown, PA (US)

(73) Assignee: DePuy Synthes Products, LLC, Raynham, MA (US)

( * ) Notice: Subject to any disclaimer, the term of this patent is extended or adjusted under 35 U.S.C. 154(b) by 583 days.

(21) Appl. No.: 12/527,055

(22) PCT Filed: Mar. 13, 2008

(86) PCT No.: PCT/US2008/056898
§ 371 (c)(1), (2), (4) Date: Aug. 13, 2009

(87) PCT Pub. No.: WO2008/112923
PCT Pub. Date: Sep. 18, 2008

(65) Prior Publication Data
US 2010/0094424 A1    Apr. 15, 2010

Related U.S. Application Data

(60) Provisional application No. 60/894,568, filed on Mar. 13, 2007.

(51) Int. Cl.
*A61F 2/44* (2006.01)
*A61F 2/28* (2006.01)
*A61F 2/30* (2006.01)

(52) U.S. Cl.
CPC ............... *A61F 2/44* (2013.01); *A61F 2/4465* (2013.01); *A61F 2002/2835* (2013.01);
(Continued)

(58) Field of Classification Search
CPC ............. A61F 2/44; A61F 2002/4627; A61F 2002/443; A61F 2002/30489; A61F 2002/3049; A61F 2002/30494; A61F 2002/30495; A61F 2002/30497; A61F 2002/30522
USPC .................. 623/17.11–17.16; 606/105, 90
See application file for complete search history.

(56) References Cited

U.S. PATENT DOCUMENTS

| 1,238,863 A | 9/1917 | Willour |
| 1,486,723 A | 3/1924 | Bernson |

(Continued)

FOREIGN PATENT DOCUMENTS

| DE | 3023942 | 1/1982 |
| DE | 3729600 | 3/1989 |

(Continued)

OTHER PUBLICATIONS

Synex System. An expandable vertebral body replacement device. Technique Guide.

(Continued)

*Primary Examiner* — Jan Christopher Merene
*Assistant Examiner* — Atiya Mahmud
(74) *Attorney, Agent, or Firm* — Baker & Hostetler LLP (57) ABSTRACT

An expandable intervertebral implant (10) includes a first member (20), a second member (40), and a collar operatively associated with the first and second members, wherein the collar includes a threaded mechanism so that rotation of the collar causes the second member to axially move with respect to the first member. The implant includes a ratchet mechanism (50, 80) so that when at least a predetermined amount of force is applied, the second member moves with respect to the first member in an axial, ratchet-type manner. The collar preferably includes a drive ring (60) rotatably attached to the first member and a ratchet ring (80) operatively associated with the drive ring. The ratchet ring includes an inner bore having at least one corresponding ratchet thread tooth form formed thereon for engaging a ratchet thread tooth form formed on the second member.

13 Claims, 9 Drawing Sheets

(52) U.S. Cl.
CPC ............... *A61F 2002/30004* (2013.01); *A61F 2002/30133* (2013.01); *A61F 2002/302* (2013.01); *A61F 2002/30235* (2013.01); *A61F 2002/30369* (2013.01); *A61F 2002/30405* (2013.01); *A61F 2002/30495* (2013.01); *A61F 2002/305* (2013.01); *A61F 2002/30507* (2013.01); *A61F 2002/30517* (2013.01); *A61F 2002/30522* (2013.01); *A61F 2002/3055* (2013.01); *A61F 2002/30565* (2013.01); *A61F 2002/30571* (2013.01); *A61F 2002/30574* (2013.01); *A61F 2002/30601* (2013.01); *A61F 2002/30604* (2013.01); *A61F 2002/30785* (2013.01); *A61F 2002/30843* (2013.01); *A61F 2002/4475* (2013.01); *A61F 2220/0025* (2013.01); *A61F 2220/0033* (2013.01); *A61F 2230/0015* (2013.01); *A61F 2230/0065* (2013.01); *A61F 2230/0069* (2013.01); *A61F 2250/0014* (2013.01); *A61F 2310/00017* (2013.01); *A61F 2310/00023* (2013.01); *A61F 2310/00179* (2013.01)
USPC ..................... 623/17.15; 623/17.16

(56) References Cited

U.S. PATENT DOCUMENTS

| | | | |
|---|---|---|---|
| 1,862,759 A | 6/1932 | Morrison | |
| 1,896,715 A | 2/1933 | Martinetti | |
| 3,426,364 A | 2/1969 | Lumb | |
| 4,401,112 A | 8/1983 | Rezaian | |
| 4,553,273 A | 11/1985 | Wu | |
| 4,554,914 A | 11/1985 | Kapp et al. | |
| 4,657,550 A * | 4/1987 | Daher | 623/17.11 |
| 4,892,546 A | 1/1990 | Kotz et al. | |
| 4,932,975 A | 6/1990 | Main et al. | |
| 5,002,576 A | 3/1991 | Fuhrmann et al. | |
| 5,192,327 A | 3/1993 | Brantigan | |
| 5,236,460 A | 8/1993 | Barber | |
| 5,290,312 A | 3/1994 | Kojimoto et al. | |
| 5,336,223 A | 8/1994 | Rogers | |
| 5,360,430 A | 11/1994 | Lin | |
| 5,405,391 A | 4/1995 | Hednerson et al. | |
| 5,443,515 A | 8/1995 | Cohen et al. | |
| 5,458,641 A | 10/1995 | Ramirez Jimenez | |
| 5,480,442 A | 1/1996 | Bertagnoli | |
| 5,489,308 A | 2/1996 | Kuslich et al. | |
| 5,571,192 A | 11/1996 | Schönhöffer | |
| 5,575,790 A | 11/1996 | Chen et al. | |
| 5,702,453 A | 12/1997 | Rabbe et al. | |
| 5,702,455 A * | 12/1997 | Saggar | 623/17.15 |
| 5,723,013 A | 3/1998 | Jeanson et al. | |
| 5,776,197 A | 7/1998 | Rabbe et al. | |
| 5,916,267 A | 6/1999 | Tienboon | |
| 5,989,290 A | 11/1999 | Biedermann et al. | |
| 6,015,436 A | 1/2000 | Schönhöffer | |
| 6,086,613 A | 7/2000 | Camino et al. | |
| 6,159,211 A | 12/2000 | Boriani et al. | |
| 6,176,881 B1 | 1/2001 | Schär et al. | |
| 6,183,517 B1 | 2/2001 | Suddaby | |
| 6,190,413 B1 | 2/2001 | Sutcliffe | |
| 6,190,414 B1 | 2/2001 | Young et al. | |
| 6,193,755 B1 | 2/2001 | Metz-Stavenhagen et al. | |
| 6,193,756 B1 | 2/2001 | Studer et al. | |
| 6,200,348 B1 | 3/2001 | Biedermann et al. | |
| 6,258,125 B1 | 7/2001 | Paul et al. | |
| 6,296,665 B1 | 10/2001 | Strnad et al. | |
| 6,344,057 B1 | 2/2002 | Rabbe et al. | |
| 6,375,683 B1 | 4/2002 | Crozet et al. | |
| 6,491,696 B1 | 12/2002 | Kunkel | |
| 6,524,341 B2 | 2/2003 | Läng et al. | |
| 6,616,695 B1 | 9/2003 | Crozet et al. | |
| 6,660,038 B2 | 12/2003 | Boyer, II et al. | |
| 6,676,703 B2 | 1/2004 | Biscup | |
| 6,730,088 B2 * | 5/2004 | Yeh | 606/247 |
| 6,752,832 B2 | 6/2004 | Neumann | |
| 6,761,738 B1 | 7/2004 | Boyd | |
| 6,808,538 B2 | 10/2004 | Paponneau | |
| 6,830,589 B2 | 12/2004 | Erickson | |
| 6,855,168 B2 | 2/2005 | Crozet | |
| 6,866,682 B1 | 3/2005 | An et al. | |
| 6,902,579 B2 | 6/2005 | Harms et al. | |
| 6,905,512 B2 | 6/2005 | Paes et al. | |
| 6,991,653 B2 | 1/2006 | White et al. | |
| 7,014,659 B2 | 3/2006 | Boyer, II et al. | |
| 7,022,138 B2 | 4/2006 | Mashburn | |
| 7,029,498 B2 | 4/2006 | Boehm et al. | |
| 7,056,343 B2 * | 6/2006 | Schafer et al. | 623/17.11 |
| 7,544,208 B1 * | 6/2009 | Mueller et al. | 623/17.15 |
| 7,641,693 B2 | 1/2010 | Gütlin et al. | |
| 7,758,648 B2 * | 7/2010 | Castleman et al. | 623/17.16 |
| 2002/0161441 A1 * | 10/2002 | Lang et al. | 623/17.11 |
| 2003/0191531 A1 | 10/2003 | Berry et al. | |
| 2004/0049270 A1 | 3/2004 | Gewirtz | |
| 2004/0078085 A1 | 4/2004 | Pointillart et al. | |
| 2004/0153160 A1 | 8/2004 | Carrasco | |
| 2004/0172129 A1 | 9/2004 | Schafer et al. | |
| 2004/0186569 A1 * | 9/2004 | Berry | 623/17.11 |
| 2004/0210312 A1 | 10/2004 | Neumann | |
| 2004/0236427 A1 | 11/2004 | Berry et al. | |
| 2005/0071007 A1 | 3/2005 | Malek | |
| 2005/0085914 A1 | 4/2005 | Lange et al. | |
| 2005/0113921 A1 * | 5/2005 | An et al. | 623/17.11 |
| 2005/0113922 A1 | 5/2005 | Brazenor | |
| 2005/0154459 A1 | 7/2005 | Wolek et al. | |
| 2005/0159814 A1 | 7/2005 | Karahalios | |
| 2005/0187634 A1 | 8/2005 | Berry | |
| 2005/0234550 A1 | 10/2005 | Metz-Stavenhagen | |
| 2006/0058877 A1 | 3/2006 | Gutlin et al. | |
| 2006/0058879 A1 | 3/2006 | Metz-Stavenhagen | |
| 2006/0084975 A1 | 4/2006 | Berry | |
| 2006/0100710 A1 * | 5/2006 | Gutlin et al. | 623/17.15 |
| 2006/0200244 A1 | 9/2006 | Assaker | |
| 2006/0241762 A1 * | 10/2006 | Kraus | 623/17.11 |
| 2006/0241770 A1 * | 10/2006 | Rhoda et al. | 623/17.15 |
| 2007/0028710 A1 | 2/2007 | Kraus et al. | |
| 2007/0255410 A1 * | 11/2007 | Dickson et al. | 623/17.11 |

FOREIGN PATENT DOCUMENTS

| | | |
|---|---|---|
| DE | 3741487 | 6/1989 |
| DE | 91 01 603.7 | 2/1991 |
| DE | 4012622 | 7/1991 |
| DE | 19509317 | 9/1996 |
| DE | 19509317 A1 | 9/1996 |
| DE | 20109599 | 8/2001 |
| DE | 10127924 | 12/2002 |
| EP | 0490159 | 6/1992 |
| EP | 0720840 | 7/1996 |
| EP | 1 188 424 | 3/2002 |
| EP | 1290993 | 3/2003 |
| JP | 2000197652 | 7/2000 |
| JP | 2000210315 | 8/2000 |
| JP | 2004-500191 A | 1/2004 |
| WO | WO 92/01428 | 2/1992 |
| WO | WO 99/63913 | 12/1999 |
| WO | WO 00/35389 | 6/2000 |
| WO | WO 01/56513 A1 | 8/2001 |
| WO | WO 2004/103225 | 12/2004 |
| WO | WO 2006/065419 A2 | 6/2006 |

OTHER PUBLICATIONS

International Search Report, issued for PCT Application No. PCT/US2008/056898, filed Mar. 13, 2008.

* cited by examiner

ADJUSTABLE INTERVERTEBRAL IMPLANT

CROSS-REFERENCE TO RELATED APPLICATIONS

This application is a national stage application under 35 USC 371 of International Application No. PCT/US2008/056898, filed Mar. 13, 2008, and claims priority to U.S. provisional patent application Ser. No. 60/894,568, filed Mar. 13, 2007, the entire content of which is hereby incorporated by reference in its entirety.

BACKGROUND OF THE INVENTION

The present invention relates to an intervertebral implant, and, more particularly, to an adjustable height intervertebral implant that preferably enables the user to adjust the height of the implant utilizing ratchet-type adjustment and screw-type adjustment.

Degenerative disc disease or degeneration of a vertebral body often results in a loss of disc height, which in turn can cause, inter alia, facet and nerve impingement. One standard of care is to replace the damaged intervertebral disc with an intervertebral implant or a damaged portion or an entire vertebral body with an intervertebral implant. That is, after removal of a damaged intervertebral disk, a damaged nucleus pulpous of an intervertebral disk or a damaged portion or entire vertebral body, an intervertebral implant is inserted into the intervertebral space of two neighboring vertebral bodies or into the space created by removal of portions of or the entire vertebral body. Preferably the intervertebral implant restores the spine as much as possible to a natural state, i.e. to restore the original height of the intervertebral disk and thus the original distance between the two neighboring vertebral bodies or vertebral bodes in various levels of the spine.

BRIEF SUMMARY OF THE INVENTION

The present invention is directed to an expandable intervertebral implant for insertion between first and second members. The implant may include a first member, a second member, and a collar operatively associated with the first and second members, the collar may include a threaded mechanism so that rotation of the collar causes the second member to axially move with respect to the first member and a ratchet mechanism so that when at least a predetermined amount of force is applied to one of or both of the first and second members, the second member moves with respect to the first member in an axial ratchet-type manner. The second member may be slightly smaller than the first member so that the second member is received at least partially within the first member.

In another exemplary embodiment, the intervertebral implant may include a first body member having a first end and a second end, wherein the first end is engageable with at least a portion of an endplate of a first vertebra. The implant may also include a second body member having a first end and a second end, wherein the first end is engageable with at least a portion of an endplate of a second vertebra. The second body member preferably includes at least one ratchet thread tooth form formed thereon. A drive ring is rotatably attached to the first body member and preferably includes an inner bore for receiving the second body member. A ratchet ring is operatively associated with the drive ring and preferably includes an inner bore having at least one corresponding ratchet thread tooth form formed thereon for engaging the ratchet thread tooth form formed on the second body member.

In use, rotation of the drive ring preferably causes rotation of the ratchet ring which in turn preferably causes the second body member to axially move with respect to the first body member. The ratchet ring is preferably radially flexible so that the ratchet thread tooth form formed on the ratchet ring is moveable to a position that disengages the ratchet thread tooth form formed on the second body member so that the second body member axially moves with respect to the first body member.

In another aspect of the present invention, an exemplary method of sizing an adjustable height intervertebral implant for implantation into an intervertebral disc space located between first and second bone members may include: (i) providing an implant having a first body member, a second body member and a collar operatively associated with the first and second body members; (ii) applying at least a predetermined amount of force to at least one of the first and second body members so that the second body member moves with respect to the first body member in an axial ratchet-type manner in order to approximate the space between the first and second bone members; and (iii) rotating the collar with respect to the second body member so that the second body member axially moves with respect to the first body member in order to fine tune the overall height of the implant to the disc space between the first and second bone members.

BRIEF DESCRIPTION OF THE SEVERAL VIEWS OF THE DRAWINGS

The foregoing summary, as well as the following detailed description of the preferred embodiments of the application, will be better understood when read in conjunction with the appended drawings. For the purposes of illustrating the adjustable intervertebral implant of the present application, there is shown in the drawings preferred embodiments. It should be understood, however, that the application is not limited to the precise arrangements and instrumentalities shown and the claims should not be limited to the embodiments shown. In the drawings:

DETAILED DESCRIPTION OF THE INVENTION

Certain terminology is used in the following description for convenience only and is not limiting. The words "right", "left", "lower" and "upper" designate directions in the drawings to which reference is made. The words "inwardly" and "outwardly" refer to directions toward and away from, respectively, the geometric center of the adjustable intervertebral implant and designated parts thereof. The words, "anterior", "posterior", "superior", "inferior" and related words and/or phrases designate preferred positions and orientations in the human body to which reference is made and are not meant to be limiting. The terminology includes the above-listed words, derivatives thereof and words of similar import.

Certain exemplary embodiments will now be described with reference to the drawings. In general, such embodiments relate to an intervertebral implant, by way of non-limiting example, an expandable intervertebral implant for implantation into a patient's spine in-between first and second adjacent or neighboring vertebrae. If used as a corpectomy device, the intervertebral implant will be able to perform single or multiple level operations, i.e., removal of one or more than one vertebra and/or portions of vertebra. The implant may be inserted between or within vertebrae, for example, portions of one or more vertebrae may be removed and the implant may contact an interior portion of the vertebra.

The intervertebral implant may have alternate applications and uses to those described herein and should not be limited to the structure or use described and illustrated. That is, while the intervertebral implant will be described as and may generally be used in the spine (for example, in the lumbar, thoracic or cervical regions), those skilled in the art will appreciate that the intervertebral implant may also be used in other parts of the body, and may have other applications outside of the medical device field.

Referring to FIGS. 1-3 and 15, the intervertebral implant 10, 210 of the first and second preferred embodiments may be constructed from any biocompatible material or combination of any biocompatible material known in the art including, but not limited to, stainless steel, titanium, titanium alloys, ceramics, polymers including, but not limited to polytetrafluoroethylene ("PTFE"), etc. Preferably, the intervertebral implant 10, 210 is constructed from polyetheretherketone ("PEEK"). The intervertebral implant 10, 210 may be radiopaque so that the placement and location of the implant can be visualized.

All components of the implant 10, 210 may be made from the same material, or, if preferred, different materials could be used, for example, to enhance durability and strength and to reduce friction and wear. In addition one or more coatings may be applied to one or more components.

Figure 1:
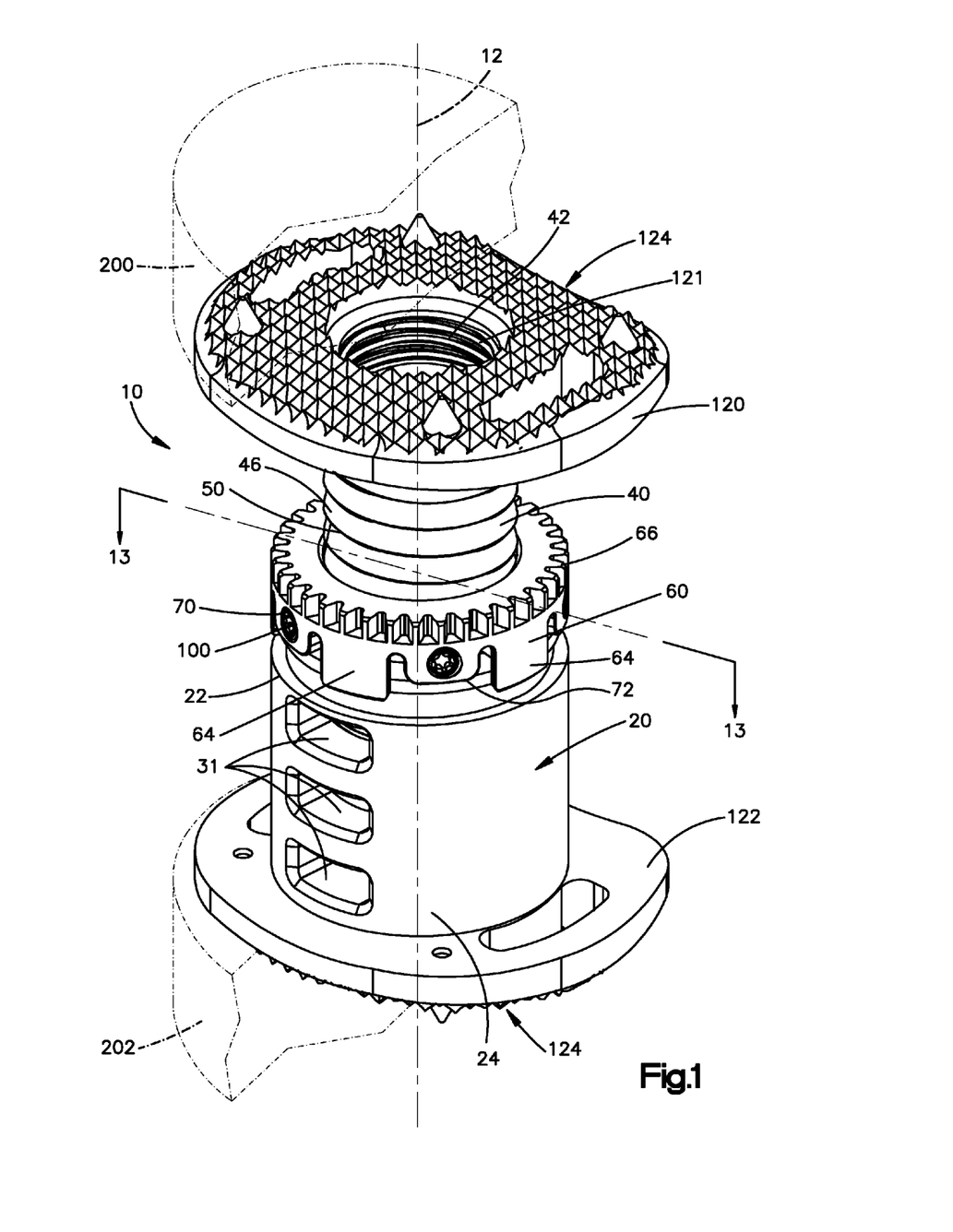
FIG. 1 is a top perspective view of an adjustable intervertebral implant in accordance with a first preferred embodiment of the present application, and arranged in an expanded position.
Figure 2:
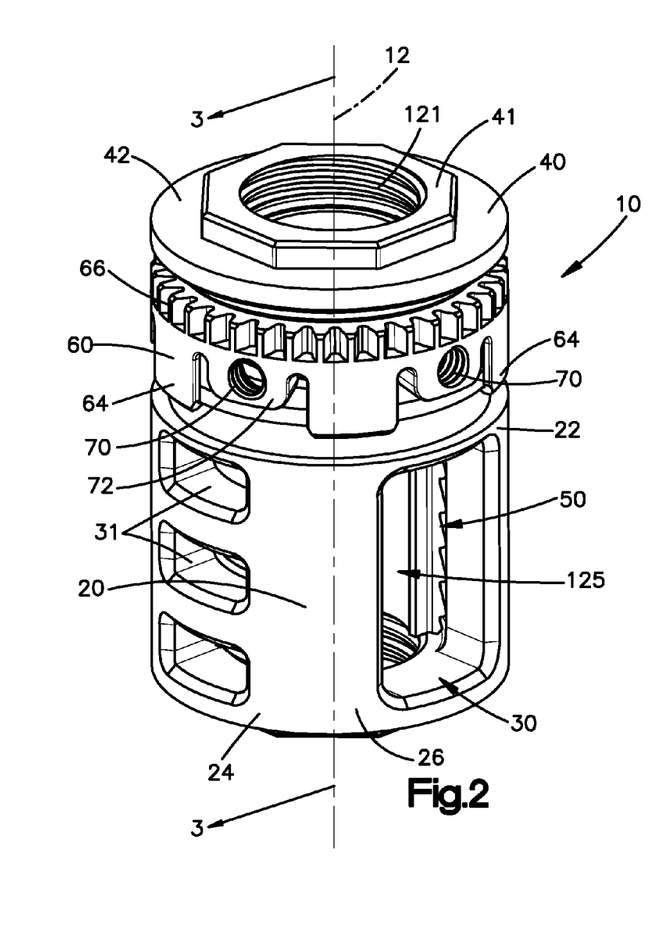
FIG. 2 is a top perspective view of a portion of the intervertebral implant shown in FIG. 1 with endplates removed for clarity, and arranged in a collapsed position.
Figure 3:
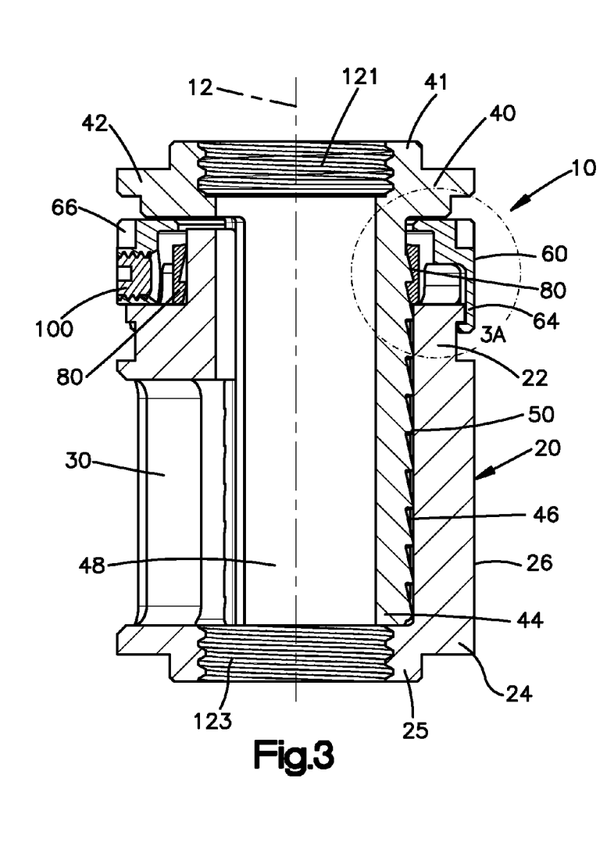
FIG. 3 is a cross-sectional view of a portion of the intervertebral implant shown in FIG. 1, taken along line 3-3 of FIG. 2, and arranged in a collapsed position.

Referring to FIGS. 1-3, the intervertebral implant 10 of the first preferred embodiment may include a first body member 20 and a second body member 40. In use, the second body member 40 is preferably sized and configured to be slightly smaller than the first body member 20 so that the second body member 40 can be moveably disposed within the first body member 20. As such, the first body member 20 will be generally characterized as an inner body member 20 while the second body member 40 will be generally characterized as an outer body member 40. However it should be noted that other arrangements of moveably associating a first body member and a second body member are contemplated. For example, the first and second body members may each include a plurality of legs extending from an end member or ring, the legs of the first member may be moveably displaceable relative to the legs of the second member.

Figure 4:
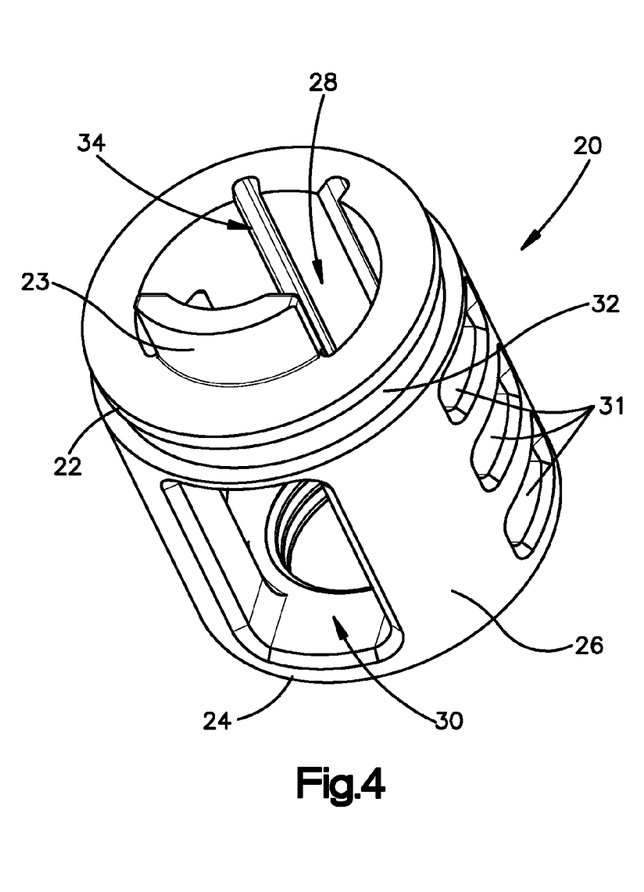
FIG. 4 is a top perspective view of a first or outer body member of the intervertebral implant shown in FIG. 1.

As best shown in FIG. 4, the outer body member 20 preferably is a substantially hollow, cylindrical member having a first end 22, a second end 24, an outer surface 26 and an internal bore 28 extending substantially from the first end 22 to the second end 24. The outer body member 20 is not limited to a cylindrical shape and may be alternatively shaped such as, for example, square, rectangular, elliptical, oval or any other shape. The outer body member 20 may also include one or more openings 30, 31 formed in the outer surface 26 thereof. In the first preferred embodiment, the outer body member 20 includes a relatively large bone packing opening 30 that preferably provides access to the internal bore 28 such that a surgeon is able to insert bone chips or alternate graft material into the implant 10, generally in an implanted configuration. The outer body member 20 also preferably includes several smaller in-growth openings 31 that permit bone in-growth in the implanted configuration to promote fusion of adjacent vertebra 200, 202. The intervertebral implant 10 is not limited to inclusion of the bone packing opening 30 or the in-growth openings 31 and may not include openings 30, 31 therein or may include additional variably shaped openings, depending upon the specific application or configuration of the implant 10.

Figure 5:
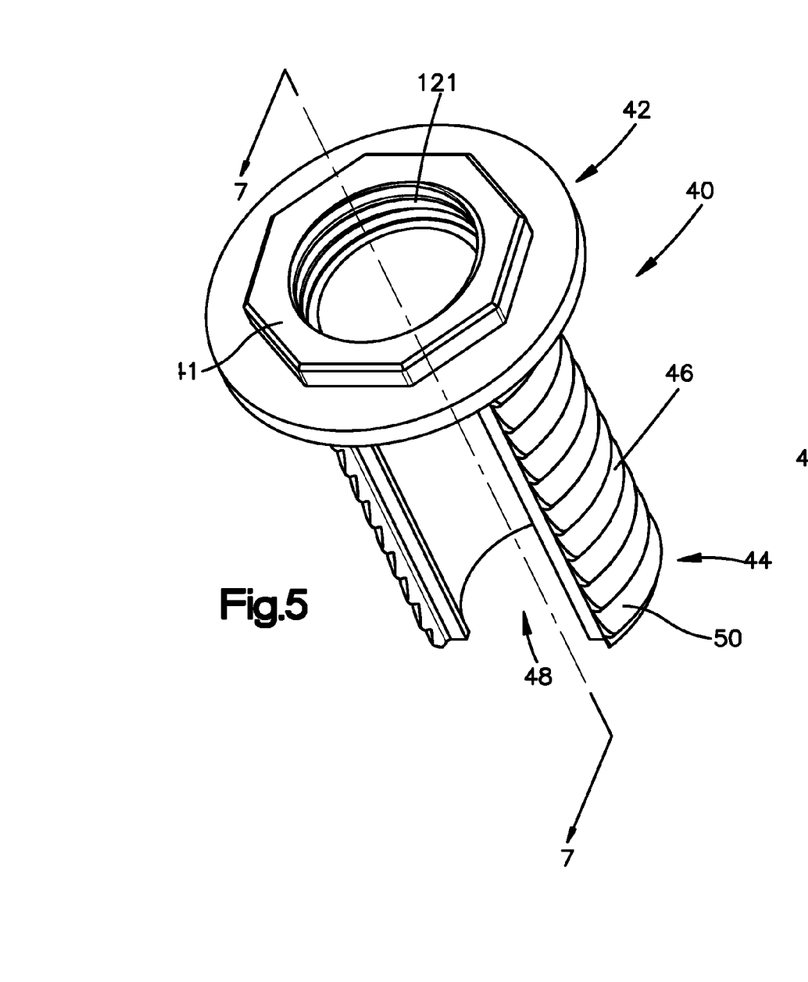
FIG. 5 is a top perspective view of a second or inner body member of the intervertebral implant shown in FIG. 1.
Figure 6:
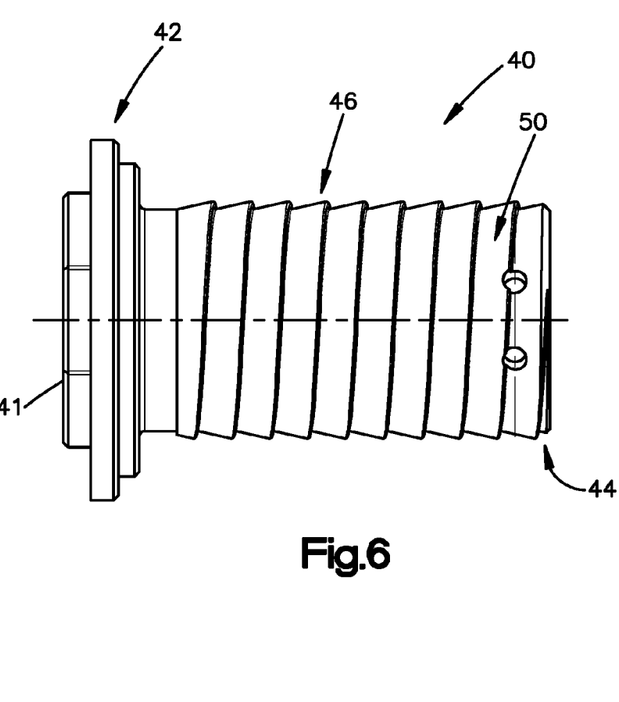
FIG. 6 is a rear elevational view of the second or inner body member shown in FIG. 5.
Figure 7:
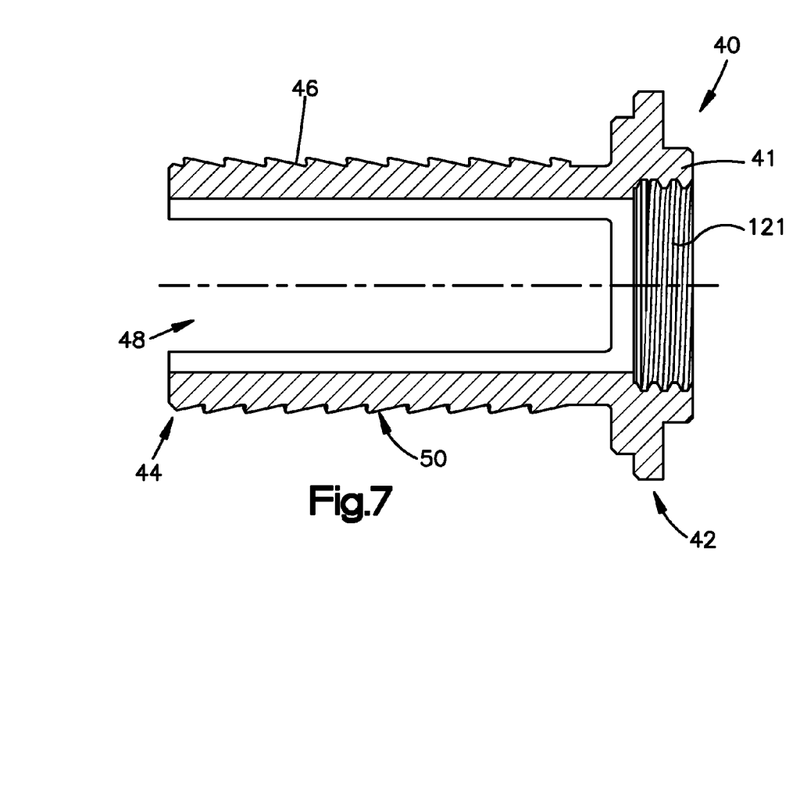
FIG. 7 is a cross-sectional view of the second or inner body member shown in FIG. 5, taken along line 7-7 of FIG. 5.

As best shown in FIGS. 5-7, the inner body member 40 preferably is in the form of a cylindrical member having a first end 42, a second end 44, an outer surface 46 and a hollow interior cavity 48. As shown, the outer surface 46 of the inner body member 40 preferably does not circumscribe 360 degrees so that the inner body member 40 is preferably in the form a partial cylindrical member. The inner body member 40 is not limited to forming only a partially cylindrical-shape and may take the form a full cylinder or may be alternatively shaped, such as square, elliptical or nearly any other shape that permits mating with the outer body member 20. The inner body member 40 may have nearly any shape that is able to withstand the normal operating conditions and perform the preferred functions of the inner body member 40, as will be described in greater detail below.

Referring to FIGS. 1-7, in the first preferred embodiment, the first end 42 of the inner body member 40 is positioned proximate a superior vertebra 200 and the second end 24 of the outer body member 20 is positioned proximate an inferior vertebra 202 in an implanted configuration. The first end 42 of the inner body member 40 and the second end 24 of the outer body member 20 do not necessarily come into facing engagement with the vertebra 200, 202, but are preferably positioned proximate the vertebra 200, 202 in the implanted configuration. For example, the first end 42 and the second end 24 may be spaced from the vertebra 200, 202 in the implanted configuration by endplates 120, 122, which are attached to the first end 42 and the second end 24, respectively, and will be described in greater detail below.

Referring to FIGS. 2 and 3, the first end 22 of the first or outer body member 20 is positioned proximate the first end 42 of the second or inner body member 40 in a collapsed position. In addition, in the collapsed position, the second end 24 of the outer body member 20 is positioned proximate the second end 44 of the inner body member 40. The implant 10 of the first preferred embodiment preferably has its smallest height in this collapsed position and may be inserted or implanted into a patient in this configuration to limit the required space needed for implantation. When the implant 10 is urged to an expanded position (FIGS. 1 and 3A), the first end 22 of the outer body member 20 is moved away from the first end 42 of the inner body member 40. In the expanded position, the implant 10 has a height greater than the height of the implant in the collapsed position. The implant 10 may take on various heights in the expanded position to accommodate various distances between the adjacent vertebrae 200, 202 or portions of the vertebrae 200, 202.

Referring to FIGS. 1-7, the outer and inner body members 20, 40 are preferably coaxially disposed along a common longitudinal axis 12 and are preferably slidably disposed (e.g., telescopic) with respect to one another so that the axial position of the inner body member 40 is adjustable with respect to the outer body member 20. The outer and inner body members 20, 40 are not limited to being telescopically and/or slidably disposed relative to each other and may be configured in nearly any manner that permits the outer and inner body members 20, 40 to move relative to each other to permit movement of the first end 42 of the inner member 40 relative to the second end 24 of the outer member 20.

The outer surface 46 of the inner body member 40 preferably includes a ratchet thread tooth form 50 formed thereon. A ratchet thread tooth form 50 refers to a structure which allows the inner body member 40 to serve as a screw-type member with respect to a ratchet ring 80, as will be described in greater detail below, when the inner body member 40 is rotated with respect to the ratchet ring 80 and also includes a cross-sectional profile which allows the inner body member 40 to move in a translational manner with respect to the ratchet ring 80 when sufficient axially force is applied in an axial direction between the inner body member 40 and the outer body member 20. It will be appreciated that axial movement may be facilitated by elastic compression of at least one of the inner body member 40 and/or the ratchet ring 80, as will be described in greater detail below. The ratchet thread tooth form may be in any form as long as it permits both axial movement and rotation.

The ratchet tooth form 50 may be, for example, a helical groove, projection or thread that allows the inner body member 40 to rotate with respect to the ratchet ring 80, the outer body member 20 or both, and further permits translation of the inner body member 40 with respect to the ratchet ring 80, the outer body member 20 or both. Although the accompanying drawings show the inner body member 40 as having a single continuous length of the ratchet thread tooth form 50, the implant 10 is not so limited. By way of example, discrete sections of the ratchet thread tooth form 50 separated by unthreaded areas may be provided, and the ratchet thread tooth form 50 may also be interrupted by one or more grooves running parallel to the longitudinal axis 12 of the implant 10.

Figure 3A:
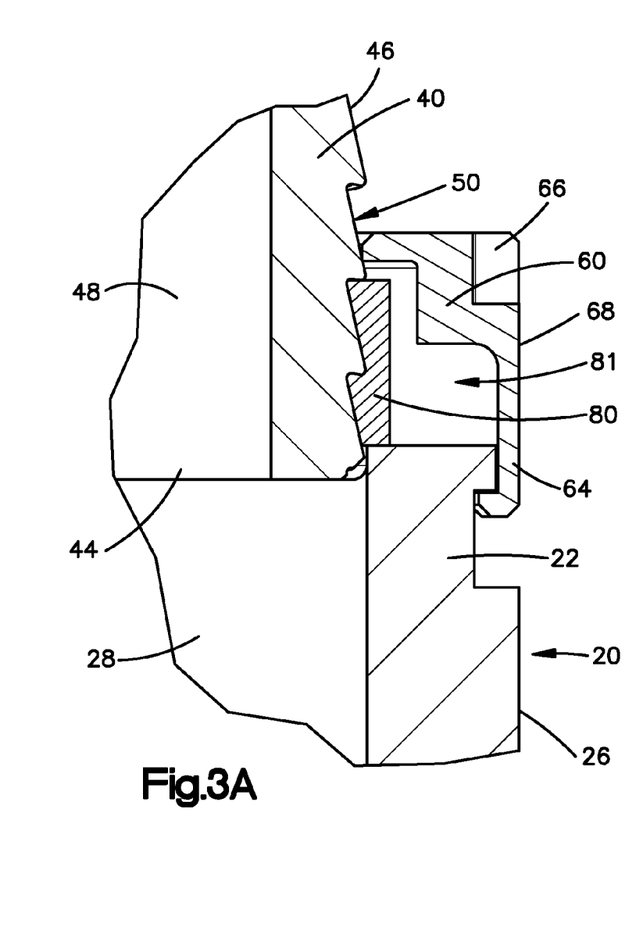
FIG. 3A is an enlarged, cross-sectional view of a portion of the intervertebral implant shown in FIG. 1, taken from within circle 3A of FIG. 3, and arranged in an expanded position.

It will be further appreciated that the pitch, profile and dimensions of the ratchet thread tooth form 50 are preferably selected to facilitate ratchet action of the implant 10 when the inner body member 40 moves with respect to the outer body member 20 preferably without rotation. By way of non-limiting example, use of a "saw tooth" thread profile may result in a "one-way" ratchet, while use of a more triangular threaded profile may allow a "two-way" ratchet, as will be understood by one having ordinary skill in the art. When undergoing ratchet type action the ratchet thread tooth form 50 may preferably slide over a corresponding ratchet thread tooth form 90 formed on the ratchet ring 80 or outer body member 20 to permit axial movement. The ratchet thread tooth form may move radially with respect to the ratchet ring 80 or outer body member 20 when the implant 10 undergoes ratchet type motion, and the radial movement of the ratchet thread tooth form may facilitate the ratchet movement. The radial movement of the ratchet thread tooth form may be provided by the elastic flexibility of the ratchet thread tooth form or the member that the ratchet thread tooth form is secured to or formed into. Alternatively, the ratchet thread tooth form may be spring biased to move radially or pivot radially with respect to the ratchet ring 80. As best shown in FIG. 3a, the ratchet thread tooth form 50 may include an undercut or negative thread angle, such as approximately 7 degrees, so that once the implant 10 is implanted the resultant compressive forces tend to cause the ratchet thread tooth form formed on the inner body member 20 to lock with the ratchet thread tooth form formed on the ratchet ring 80.

Referring to FIGS. 8A-13, the intervertebral implant 10 may also include a drive ring 60 disposed between the outer and inner body members 20, 40 and a ratchet ring 80 associated with and preferably contained within the drive ring 60. Although the drive ring 60 and the ratchet ring 80 will be generally described as two separate and independent components, it is envisioned that the drive ring 60 and the ratchet ring 80 may be integrally formed as a single component or may be constructed as an assembly of several components, depending upon the operation and/or preferred use of the implant 10. The drive ring 60 and ratchet ring 80 preferably interact with the outer and inner body members 20, 40 to permit axial manipulation or modification of the height of the implant 10 through a screw-type adjustment and a ratchet-type adjustment, which will be described in greater detail below.

Figure 8A:
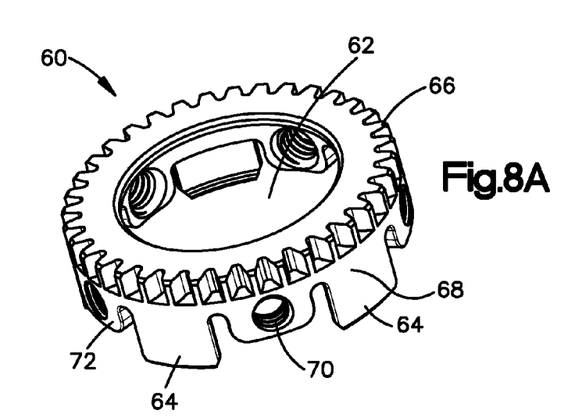
FIG. 8A is a top perspective view of a drive ring of the intervertebral implant shown in FIG. 1.
Figure 8B:
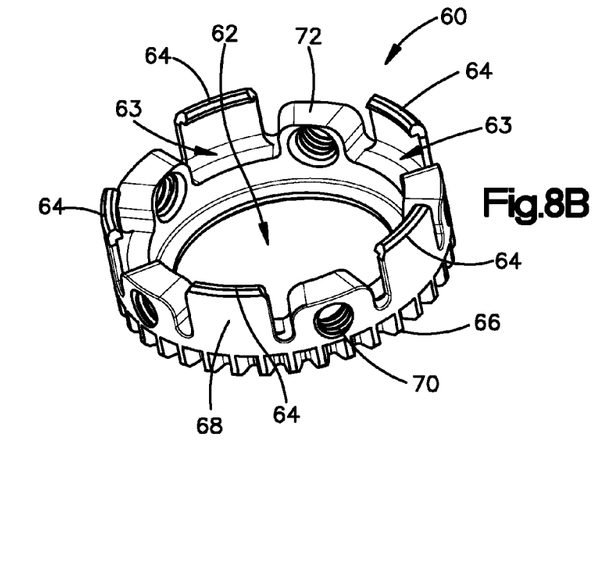
FIG. 8B is a bottom perspective view of the drive ring shown in FIG. 8A.
Figure 9:
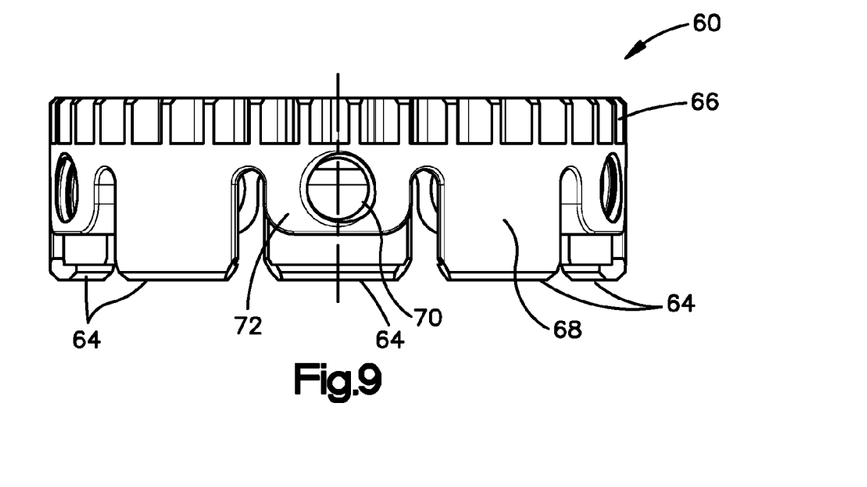
FIG. 9 is a side elevational view of the drive ring shown in FIG. 8A.
Figure 10:
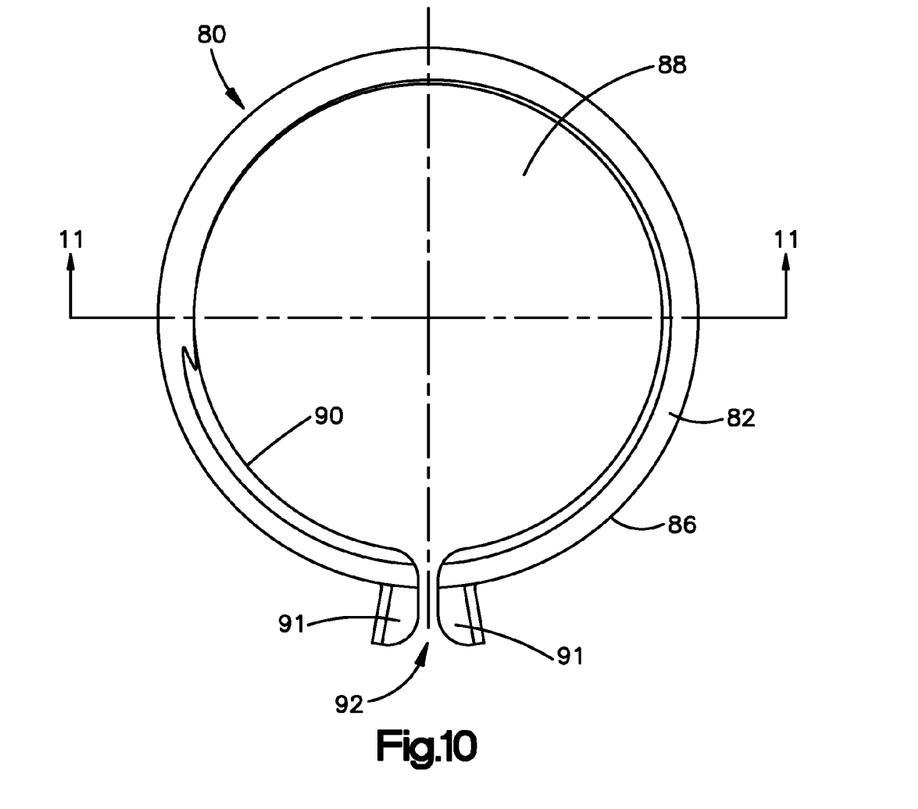
FIG. 10 is a top plan view of a ratchet ring of the intervertebral implant shown in FIG. 1.
Figure 11:
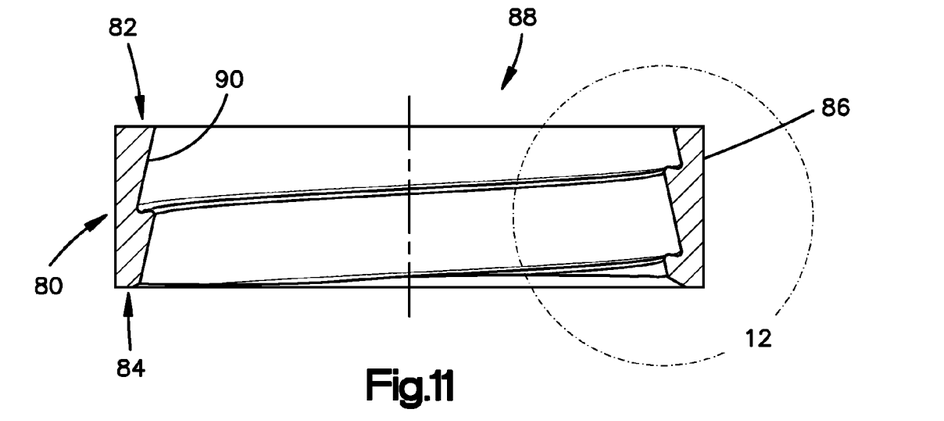
FIG. 11 is a cross-sectional view of the ratchet ring shown in FIG. 10, taken along line 11-11 of FIG. 10.
Figure 12:
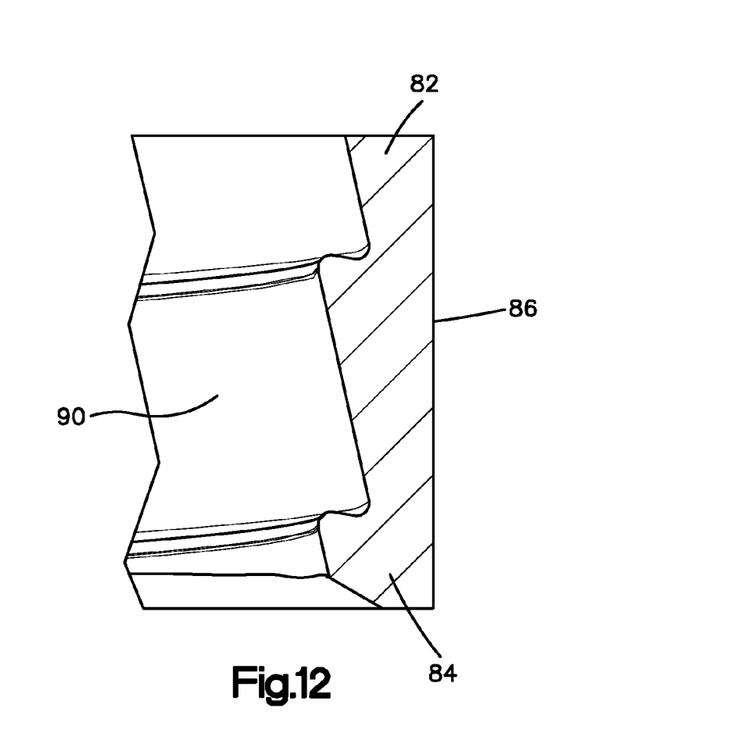
FIG. 12 is an enlarged, cross-sectional view of the ratchet ring shown in FIG. 10, taken from within circle 12 of FIG. 11.

As best shown in FIGS. 8A and 8B, the drive ring 60 may include an inner bore 62 within which the inner body member 40 is received in an assembled configuration. The drive ring 60 is also preferably moveably coupled, more preferably rotatably attached, to the outer body member 20. The drive ring 60 may be connected to the outer body member 20 by any means that enables the drive ring 60 to be moveably coupled, preferably rotatably attached, to the outer body member 20 including, but not limited to a snap-fit connection, a press-fit connection, etc. The drive ring 60 preferably includes one or more projections 64 for engaging a circumferential groove 32 formed on the outer body member 20. In the first preferred embodiment, the drive ring 60 includes five (5) projections 64 that are generally evenly, radially spaced about the circumference of the ring 60. The outer body member 20 also preferably includes an alignment projection 23 that interacts with the inner body member 40 to generally axially align the inner body member 40 with the outer body member 20 as the components axially move relative to each other.

The drive ring 60 may also include a ring gear 66 formed on a surface thereof. As shown, the ring gear 66 may be formed along an outer surface 68 of the drive ring 60. The ring gear 66 is preferably configured to cooperate with a corresponding tool such as, for example, a pinion (not shown) so that rotation of the pinion, which may be connected to a hand tool, power tool, etc., results in rotation of the drive ring 60. In this manner, the ring gear 66 helps facilitate rotation of the drive ring 60. Alternatively and/or in addition, the drive ring 60 may be rotated manually without the aid of the ring gear 66 and pinion, or by any other means now or hereafter known.

As best shown in FIGS. 10-13, the ratchet ring 80 may include a first end 82, a second end 84, an outer surface 86, an inner bore 88 extending from the first end 82 to the second end 84, and at least one threaded mechanism or ratchet thread tooth form 90 formed on the inner surface of the inner bore 88 for engaging the ratchet thread tooth form 50 formed on the outer surface 46 of the inner body member 40. The ratchet ring 80 is preferably contained within and coupled to the drive ring 60 so that rotation of the drive ring 60 causes simultaneous rotation of the ratchet ring 80.

The ratchet ring 80 also preferably includes at least one slot 92 so that the ratchet ring 80 is flexible so that when the ratchet ring 80 is subjected to at least a predetermined amount of axial force such as, for example, by a force intended to axially separate the outer and inner body members 20, 40, the ratchet ring 80 can radially expand in order to allow the inner body member 40 to axially translate with respect to the ratchet ring 80, as will be described in greater detail below. Although it is envisioned that the ratchet ring may take other forms, for example, the ratchet ring may be a continuous expandable ring, the ring could be expandable by, for example, its material and/or its configuration. Preferably, the ratchet ring 80 is resilient or configured to generally return to its original size and/or shape once the axial force has been removed so that the ratchet thread tooth form 90 formed on the inner bore 88 of the ratchet ring 80 re-engages the ratchet thread tooth form 50 formed on the outer surface 46 of the inner body member 40 to generally secure the axial position of the inner body member 20 relative to the outer body member 40.

Referring to FIGS. 3A, 8B, 10 and 13, in the first preferred embodiment, the ratchet ring 80 is mounted in a cavity 81 defined by the first end 22 of the outer body member 20, the ratchet thread tooth form 50 of the inner body member 40 and an inner surface of the drive ring 60. The ratchet ring 80 preferably includes ears 91 that extend radially outwardly from the ratchet ring 80 at the slot 92 and are positioned in ratchet alignment gaps 63 defined between downwardly depending legs 72 of the drive ring 60. The drive ring 60 of the first preferred embodiment includes five (5) downwardly depending legs 72, thereby defining five (5) alignment gaps 63 such that the ears 91 may be positioned in any of the alignment gaps 63 in the assembled configuration. The ratchet ring 80 is not limited to being mounted in the cavity 81 such that the ears 91 are positioned in the alignment gaps 63 and may be coupled to the drive ring 60 and in the implant 10 by any number of mechanical structures that permit interengagement of the ratchet ring 80 with the ratchet tooth form 50.

Referring to FIGS. 1-13, in use, as will be described in greater detail below, the outer body member 20, drive ring 60 and ratchet ring 80 are preferably configured to remain in the same relative axial position relative to each other, while the drive ring 60 and ratchet ring 80 are both generally free to rotate relative to the outer body member 20. That is, the drive ring 60 and ratchet ring 80 are preferably configured so that they are generally axially fixed but rotationally movable with respect to the outer body member 20. Meanwhile, the inner body member 40 is preferably configured to axially translate with respect to the outer body member 20, drive ring 60 and ratchet ring 80 based upon manipulation of the implant 10 by the user. In addition, the inner body member 40 is preferably configured to move axially, but generally not rotate with respect to the outer body member 20. In this manner, as will be generally appreciated by one of ordinary skill in the art, rotation of the drive ring 60, and hence the ratchet ring 80 which is preferably coupled thereto, causes the inner body member 40 to axially move with respect to the drive ring 60 and ratchet ring 80, and hence with respect to the outer body member 20.

Prevention of relevant rotation of the inner body member 40 with respect to the outer body member 20 may be accomplished by any means now or hereafter known in the art including, but not limited to, for example, forming one or more guide slots 34 (FIG. 4) on the inner surface of the outer body member 20. The guide slots 34 preferably extend parallel to the longitudinal axis 12, while the inner body member 40 may include one or more pins or ribs (not shown) for cooperating with the one or more guide slots 34 formed in the outer body member 20 in order to prevent or generally limit rotation of the inner body member 40 with respect to the outer body member 20. The one or more pins or ribs may be integrally formed with the inner body member 40 or may be a separate component and joined thereto. Alternatively, the inner body member 40 may include one or more guide slots and the outer body member 20 may include one or more pins or ribs. Alternatively, any other mechanism for preventing or generally limiting relative rotation between the outer and inner body members 20, 40 may be used including, but not limited to, corresponding non-circular shapes, such as square, oval, elliptical, etc.

Figure 13:
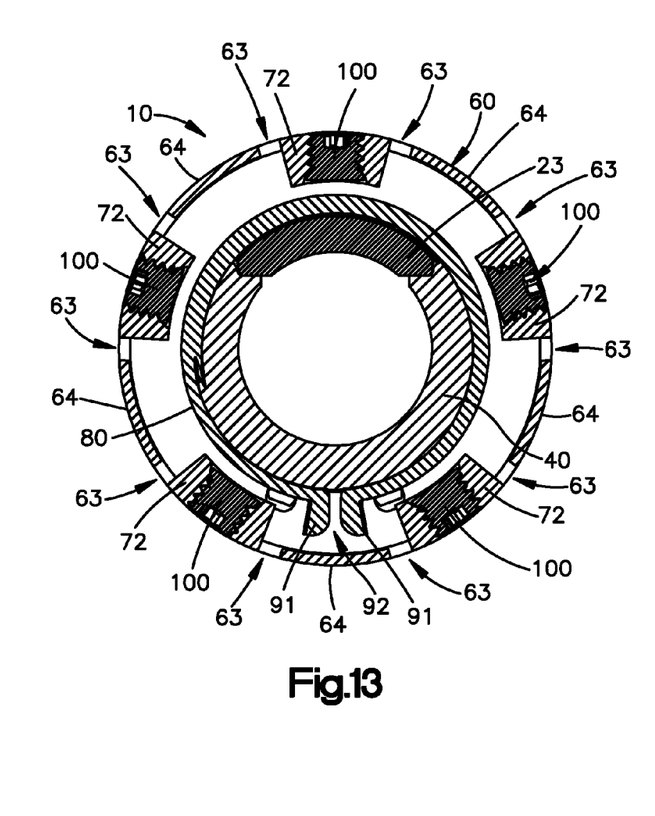
FIG. 13 is a cross-sectional view of the intervertebral implant shown in FIG. 1, taken along line 13-13 of FIG. 1.

Rotation of the drive ring 60, and hence of the ratchet ring 80 which is coupled thereto, preferably activates the threaded feature formed on the intervertebral implant 10. That is, as a result of the drive ring 60 being rotated relative to the inner and outer body members 40, 20, the ratchet ring 80 is preferably simultaneously rotated, which in turn, as a result of the interaction of the corresponding ratchet thread tooth form 50 formed on the outer surface 46 of the inner body member 40 and the ratchet thread tooth form 90 formed on the inner surface of the ratchet ring 80, causes the inner body member 40 to axially move with respect to the drive ring 60 and ratchet ring 80, and hence with respect to the outer body member 20. Referring specifically to FIG. 13, when the drive ring 60 is initially rotated, the ratchet ring 80 does not rotate until one of the ears 91 impacts an adjacent downwardly depending leg 72. When one of the ears 91 comes into contact with one of the downwardly depending legs 72, the drive ring 60 and the ratchet ring 80 rotate together due to the downwardly depending leg 72 pushing the ear 91 and the ratchet ring 80 in the rotation direction. If the user reverses the rotation of the drive ring 60 relative to the ratchet ring 80, the ratchet ring 80 will not rotate with the drive ring 60 until the opposite downwardly depending leg 72 on the opposite side of the cavity 63 impacts the adjacent ear 91, thereby urging the ratchet ring 80 to rotate through contact between the downwardly depending leg 72 and the ear 91. Accordingly, during initial rotation, there may be some "play" in the relative rotation between the drive ring 60 and the ratchet ring 80 until one of the ears 91 comes into contact with one of the downwardly depending legs 72. Preferably, the threaded mechanism enables the drive ring 60 to be rotatably driven in either direction, so that the intervertebral implant 10 can be expanded or contracted. Thus, in use, the outer and inner body members 20, 40 can be expanded and/or contracted via rotation of the drive ring 60 and the ratchet ring 80.

In addition, as will be generally appreciated by one of ordinary skill in the art, the intervertebral implant 10 also preferably provides the user with the ability to apply an axial or separation load, for example, manually or with the aid of a surgical tool, to the intervertebral implant 10 in order to expand and/or contract the intervertebral implant 10 via a ratcheting feature. That is, the outer and inner body members 20, 40 can be expanded and/or contracted via a ratchet type mechanism by the application of an axial force. By applying a sufficient axial separating force to the intervertebral implant 10, for example, an axial force to the inner body member 40 and an equal and opposite axial force to the outer body member 20, the ratchet ring 80 will flex and/or deflect outwards enabling the ratchet thread tooth form 50 formed on the outer surface 46 of the inner body member 40 to move over and/or across the corresponding ratchet thread tooth form 90 formed on the inner surface of the ratchet ring 80 so that the inner body member 40 can axially translate or telescope with respect to the drive ring 60 and ratchet ring 80, and hence with respect to the outer body member 20. As the ratchet ring 80 expands to accommodate the engagement of the peaks of ratchet tooth forms 50, 90 or to permit the peaks to slide over each other during the ratchet-type adjustment, the ears 91 are permitted to expand within the cavities 63, at least until the ears 91 come into contact with the adjacent downwardly depending legs 72.

In the first preferred embodiment, the ratchet ring 80 of the implant 10 provides a majority of the flexure to accommodate the ratchet-type adjustment of the implant, as was described above. However, the implant is not so limited and each or a combination of both of the ratchet ring 80 and/or the inner body member 40 may flex during the ratcheting operation to permit the teeth of the ratchet thread tooth forms 90, 50 to slide over each other and flex back into engagement as the inner and outer body members 40, 20 are axially moved relative to each other utilizing the ratcheting-type movement.

Thus, axial adjustment of the inner and outer body members 40, 20 can be achieved by the ratchet-type adjustment or the screw-type adjustment, depending upon the preference of the user. For example, rough spacing of the outer body member 20 relative to the inner body member 40 may be accomplished through the ratchet-type adjustment, while fine adjustment of the axial offset of the outer body member 20 relative to the inner body member 40 may be accomplished through screw-type adjustment described above.

Using the intervertebral implant 10 in the ratchet mode generally enables faster, generally rough, expansion/contraction of the intervertebral implant 10. In addition, using the implant 10 in the ratchet mode preferably permits macro or large scale changes in the overall size of the intervertebral implant 10. In contrast, using the implant 10 in the threaded or screw-type mode may provide the user with the ability to adjust the size of the intervertebral implant 10 infinitely or in a relatively fine manner. In addition, expansion/contraction by rotating the drive ring 60 may be more precise, and thus enable the user to fine tune the overall height of the implant 10. The implant 10 preferably enables the user to switch between the ratchet-type and screw-type adjustment modes at any time according to user preference.

The ratchet thread tooth form 50 formed on the inner body member 40 and the corresponding ratchet thread tooth form 90 formed on the inner surface of the ratchet ring 80 may be constructed to be self-locking so that the position of the inner body member 40 can be fixed with respect to the outer body member 20 without the need for any additional locking mechanism. Alternatively, the intervertebral implant 10 may also include a locking mechanism for fixing the position of the outer body member 20 with respect to the inner body member 40 once a desired implant height has been achieved by the user using the ratchet-type or screw-type adjustment. For example, as best shown in FIGS. 1-3, the drive ring 60 may include one or more threaded bores 70 formed on the downwardly depending legs 72 for threadably receiving one or more set screws 100. To secure the drive ring 60 relative to the ratchet ring 80 and, generally, the inner body member 40 relative to the outer body member 20, one or more of the set screws 100 is driven into one of the threaded bores 70 until the tip of the set screw 100 contacts and urges the outer surface 86 of the ratchet ring 80 toward the inner body member 40, which generally secures the movement of the ratchet ring 80 relative to the drive ring 60 by urging the ratchet thread tooth form 90 of the ratchet ring 80 into engagement with the ratchet thread tooth form 46 of the inner body member 40. Such engagement generally prevents a user from rotating the drive ring 60 and the ratchet ring 80, due to the engagement of the ratchet thread tooth forms 90, 50. In addition, rotational engagement of the set screws 100 in the threaded bores 70 generally limits the ability of the ratchet ring 80 to expand and thus, generally prevents the inner body member 40 from moving with respect to the outer body member 20 via the ratchet-type adjustment.

One or more of the set screws 100 may be tightened into the threaded bores 70 in the assembled configuration to generally lock the outer body member 20 relative to the inner body member 40, however, in the preferred embodiment, a surgeon typically tightens only one of the set screws 100, which is facing the surgeon after arranging the implant 10 in the implanted position between the vertebra 200, 202. Alternatively, any other locking mechanism may be used, for example, the set screw 100 may contact the inner or outer body members 40, 20, which in turn would generally prevent the drive ring 60 and ratchet ring 80 from rotating and the inner and outer body members 40, 20 from axially moving relative to each other or nearly any other locking mechanism that limits movement of the outer and inner body members 20, 40 relative to each other may be utilized, such as external clamping, fastening, adhesive bonding or related mechanisms and methods.

Figure 14:
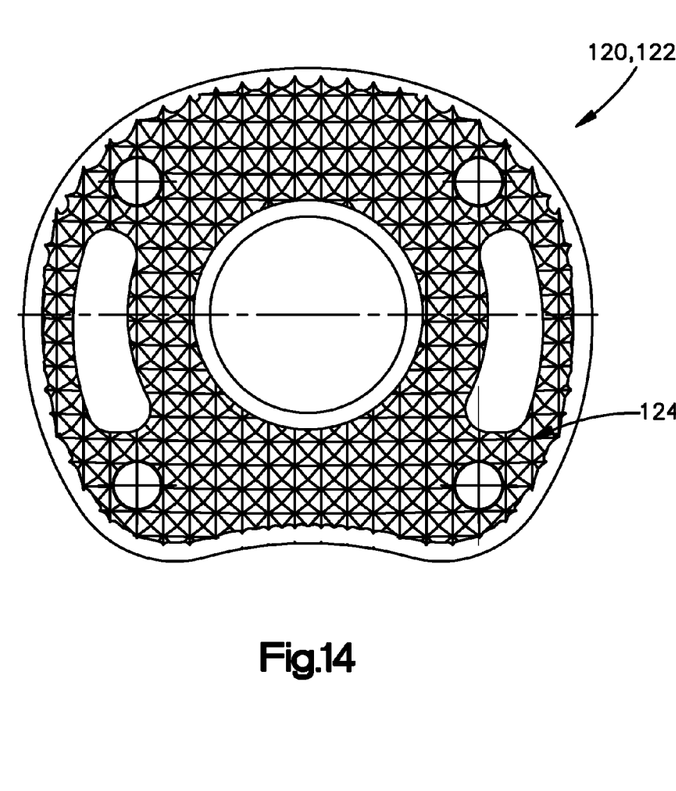
FIG. 14 is a top plan view of an endplate of the intervertebral implant shown in FIG. 1.

As best shown in FIGS. 1 and 14, the outer and inner body members 20, 40 may include endplates 120, 122 mounted thereto, respectively, for contacting at least a portion of the endplate of the adjacent vertebrae. The endplates 120, 122 may be formed as a separate and distinct component, and may be connected to the outer and inner body members 20, 40 by any means known in the art, including, but not limited to, interference-fit, press-fit, threading, screwing, bonding, set screw, etc. In this manner, the intervertebral implant 10 can be provided in a kit with a plurality of different endplates 120, 122 thus enabling the user to select the desired endplates 120, 122 that best conforms with the contours of the patient's vertebral endplates. By way of example, various endplates 120, 122 may be provided that include varying shapes including, but not limited to, circular, square, rectangular, oval, kidney-shaped, etc. and/or one or more of the following characteristics: a generally wedge-shaped surface, curved surface, flat surface, etc. Alternatively, the upper and lower endplates 120, 122 may be integral formed with the outer and inner body members 20, 40. In the first preferred embodiment, the endplates 120, 122 initially engage with an octagonal projection 41, 25 at the ends 42, 24 of the outer and inner body members 20, 40, respectively and are secured to the outer and inner body members 20, 40 using a locking screw (not shown) that engages an internal thread 121, 123 on the outer and inner body members 20, 40. Alternatively, the projection 41, 25 can have external threads and the endplate can have a bore or cavity that fits over the projection and a set screw with internal threads for engaging the threads formed on the projection to secure the position of the endplates with respect to the outer and inner body members 20, 20. The octagonal projections 41, 25 permit at least eight (8) orientations of the endplates 120, 122 relative to the outer and inner body members 20, 40. While an octagon projection has been shown and described it is appreciated that a circular, elliptical, square or any other shape may be used.

The endplates 120, 122 preferably include one or more fixation members 124 for contacting and/or engaging the endplates of the adjacent vertebrae 200, 202. The fixation members 124 may be any form known including, but not limited to, a plurality of protrusions, a plurality of undulating structures, a plurality of projections, a plurality of ridges, a plurality of teeth, one or more keels, etc. The endplates 120, 122 may also be configured to receive one or more bone fixation elements, such as, for example, screws, pins, etc. for securing the endplates 120, 122 to the patient's vertebrae.

As previously mentioned, the outer body member 20 may include one or more openings 30, 31. The inner body member 40 may be in the form of a partial cylindrical surface (e.g., the walls of the inner body member 40 preferably do not circumscribe 360 degrees) so that a window 125, comprised of the bone packing opening 30 and the partial opening in the inner body member 40, is formed in the intervertebral implant 10 for delivering bone chips or other similar material into the cavity 48 of the inner body member 40. In addition, the outer and inner body members 20, 40 and the endplates 120, 122 are preferably open at their ends proximate the engagement with the vertebra 200, 202 such that the bone chips or other material may come into facing engagement with the vertebra 200, 202 or physically communicate with the vertebra 200, 202 through the holes in the implant 10.

In the first preferred embodiment, the drive ring 60 and the ratchet ring 80 comprise a collar that is rotatably mounted to the outer body member 20. The ratchet ring 80 includes the ratchet thread tooth form 90 that engages the ratchet thread tooth form 50 on the outer surface 46 of the inner body member 40. The engagement of the ratchet thread tooth form 90 of the ratchet ring 80 and the ratchet thread tooth form 50 of the inner body member 40 permits axial movement of the inner body member 40 relative to the outer body member 20 by rotating the collar relative to the outer and inner body members 20, 40 in a screw-type manner or adjustment. The collar also includes a ratchet mechanism that is comprised of the interaction of the ratchet ring 80 and the inner body member 40 in the first preferred embodiment. Specifically, the ability of the ratchet ring 80 to radially expand such that the peaks of the ratchet thread tooth form 90 are able to axially move past the ratchet thread tooth form 50 of the inner body member 40 through the application of a predetermined axial force applied between the outer and inner body members 20, 40 permits the outer and inner body members 20, 40 to move with respect to each other in an axial ratchet-type manner.

Figure 15:
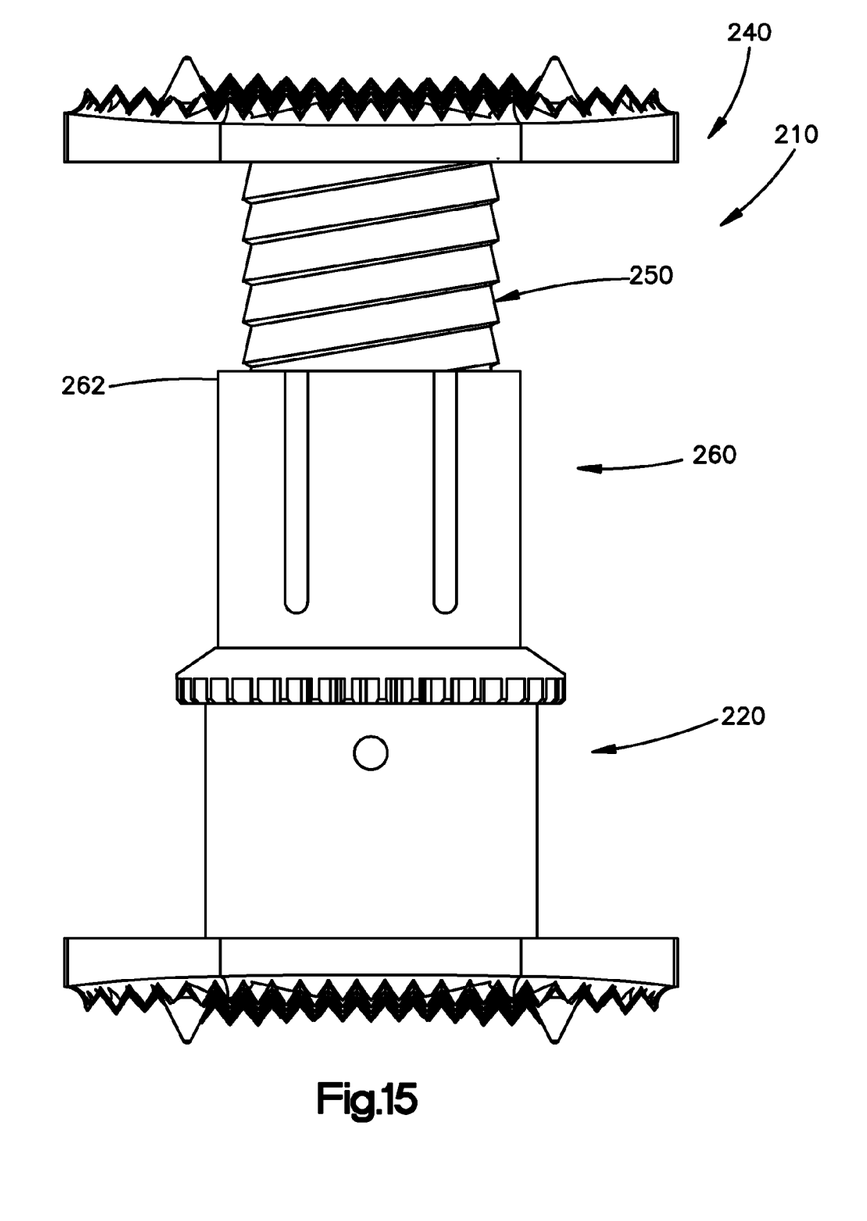
FIG. 15 is a side elevational view of an adjustable intervertebral implant in accordance with a second preferred embodiment of the present application.

Referring to FIG. 15, in a second preferred embodiment of the present application, an intervertebral implant 210 is substantially similar to implant 10 of the first preferred embodiment and like components and features will generally not be described again herein. The intervertebral implant 210 may include an outer body member 220, an inner body member 240, and a cantilever spring gear 260. Alternatively, it is envisioned that the outer body member 220 may be integrally formed with the cantilever spring gear 260. Similar to the inner body member 40 of the first preferred embodiment of the implant 10, the inner body member 240 preferably includes a ratchet thread tooth form 250 formed on an outer surface thereof.

The outer body member 220 and the cantilever spring gear 260 are preferably configured in a manner which maintains their relative axial position but which enables the cantilever spring gear 260 to rotate relative to and preferably about the axis of the outer body member 220. The cantilever spring gear 260 preferably includes a ratchet thread tooth form (not shown) formed in an inner surface that is configured to substantially correspond to or mate with the ratchet thread tooth form 250 formed on an outer surface of the inner body member 240 so that rotation of the cantilever spring gear 260 causes the inner body member 240 to axially move with respect to the cantilever spring gear 260, and hence with respect to the outer body member 220. The ratchet thread tooth form may be in the form of a ledge or projection formed at the tip 262 of the cantilever spring gear 260.

In use, rotation of the cantilever spring gear 260 with respect to the outer body member 220 activates the threaded feature formed on the intervertebral implant 210, which in turn results in the inner body member 240 axially moving with respect to the cantilever spring gear 260, and hence the outer body member 220. That is, the intervertebral implant 210 can be expanded or contracted using the ratchet thread tooth form 250 formed on an outer surface of the inner body member 240 by rotating the cantilever spring gear 260. As the cantilever spring gear 260 rotates, the tip of the cantilever spring engages the ratchet thread tooth form 250 formed on the inner body member 240 and follows along the thread to drive the implant 210 to expand or contract.

In addition, as will be generally appreciated by one of ordinary skill in the art, the intervertebral implant 210 also preferably provides the user with the ability to apply an axial separating load to the intervertebral implant 210 in order to expand and/or contract the intervertebral implant 210 via a ratcheting feature. That is, the outer and inner body members 220, 240 can be expanded and/or contracted via a ratchet type mechanism by the application of an axial force. By applying a sufficient axial force to the intervertebral implant 210, the inner body member 240 will axially translate as the cantilever spring gear 260 moves relative to and over the ratchet thread tooth form 250 formed on the outer surface of the inner body member 240 and deflect outwards to provide room for the ratchet thread tooth form 250 of the inner body member 240 to pass axially. The cantilever spring gear 260 preferably is configured to return to its original geometry once the axial force has been removed so that the cantilever spring gear 260 re-engages the ratchet thread tooth form 250 formed on the outer surface of the inner body member 240 at a different position.

While the foregoing description and drawings represent the preferred embodiments of the present invention, it will be understood that various additions, modifications, combinations and/or substitutions may be made therein without departing from the spirit and scope of the invention as defined in the accompanying claims. In particular, it will be apparent to those skilled in the art that the invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components, which are particularly adapted to specific environments and operative requirements without departing from the principles of the invention. In addition, features described herein may be used singularly or in combination with other features. The presently disclosed embodiments are, therefore, to be considered in all respects as illustrative and not restrictive, the scope of the invention being indicated by the appended claims, and not limited to the foregoing description.

What is claimed is:

1. An expandable intervertebral implant that is configured to be disposed between first and second vertebrae, the expandable intervertebral implant comprising:

a first body member defining an axis, a first end, and a second end spaced from the first end of the first body member along the axis in an axial direction;

a second body member having a first end and a second end, the second end of the second body member spaced from the first end of the second body member along the axial direction, the first end of the first body member positioned proximate the first end of the second body member in a collapsed position, the second body member including a ratchet portion comprising at least one first ratchet thread tooth form formed thereon;

a ratchet ring carried by the first body member, the ratchet ring defining an inner bore that extends along the axis in the axial direction, and at least one slot configured to allow radial movement of the ratchet ring in a radial direction outwardly away from the axis, the ratchet ring having at least one second ratchet thread tooth form formed around the inner bore of the ratchet ring, the at least one second ratchet thread tooth form threadedly mated with the at least one first ratchet thread tooth form such that rotation of the ratchet ring causes the second body member to move in the axial direction with respect to the first body member while the first body member remains stationary in the axial direction relative to the ratchet ring, and an application of an axial force between the ratchet ring and the second body member causes the at least one first ratchet thread form to slide axially over the at least one second ratchet thread tooth form so that the second body member moves in the axial direction relative to the first body member; and a drive ring coupled to the ratchet ring such that rotation of the drive ring causes rotation of the ratchet ring, the drive ring defines a drive inner bore that receives at least a portion of the ratchet ring, wherein the drive ring includes a plurality of projections configured to mate with a circumferential groove formed on an outer surface of the first body member proximate the first end of the first body member.

2. The implant of claim 1, wherein the ratchet ring comprises a pair of ears that attaches to the drive ring.

3. The implant of claim 2, wherein the at least one slot is located between the ears.

4. The implant of claim 1, further comprising:
a locking mechanism configured to fix a position of the first body member with respect to the second body member, the locking mechanism including a plurality of set screws configured to threadingly engage a corresponding plurality of screw holes in the drive ring.

5. The implant of claim 1, wherein the ratchet portion of the second body member defines an outer dimension that is slightly smaller than an inner dimension defined by an inner surface of the first body member so that the second body member is at least partially received within the first body member.

6. The implant of claim 1, wherein the first body member is substantially cylindrical and defines an internal cavity, the second body member is a substantially cylindrical and includes an outer surface, the outer surface of the second body member including the at least one first ratchet thread tooth form that is threadedly mated with the at least one second ratchet thread tooth form, the outer surface of the second body member is slidably receivable within the internal cavity of the first body member.

7. The implant of claim 1, wherein the second end of the second body member is positioned proximate to the first end of the first body member in an expanded position member.

8. The implant of claim 1, wherein the first body member includes a first endplate that is configured to contact the first vertebra and the second body member includes a second endplate that is configured to contact the second vertebra, the first and second endplates are removeably coupled to the first and second body members, respectively.

9. The implant of claim 1, the drive inner bore receives at least a portion of the second body member.

10. A method of sizing an adjustable height intervertebral implant, the intervertebral implant including a first body member defining an axis, a first end, and a second end spaced from the first end of the first body member along the axis in an axial direction;

a second body member having a first end and a second end, the second end of the second body member spaced from the first end of the second body member along the axial direction, the first end of the first body member positioned proximate the first end of the second body member in a collapsed position, the second body member including a ratchet portion comprising at least one first ratchet thread tooth form formed thereon;

a ratchet ring carried by the first body member, the ratchet ring defining an inner bore that extends along the axis in the axial direction, and at least one slot configured to allow radial movement of the ratchet ring in a radial direction outwardly away from the axis, the ratchet ring having at least one second ratchet thread tooth form formed around the inner bore of the ratchet ring, the at least one second ratchet thread tooth form threadedly mated with the at least one first ratchet thread tooth form such that rotation of the ratchet ring causes the second body member to move in the axial direction with respect to the first body member while the first body member remains stationary in the axial direction relative to the ratchet ring, and an application of an axial force between the ratchet ring and the second body member causes the at least one first ratchet thread form to slide axially over the at least one second ratchet thread tooth form so that the second body member moves in the axial direction relative to the first body member; and a drive ring coupled to the ratchet ring such that rotation of the drive ring causes rotation of the ratchet ring, the drive ring defines a drive inner bore that receives at least a portion of the ratchet ring, wherein the drive ring includes a plurality of projections configured to mate with a circumferential groove formed on an outer surface of the first body member proximate the first end of the first body member, the method comprising:
a) applying a force in the axial direction to the first and second body members so that the second body member moves with respect to the first body member such that the at least one first ratchet thread tooth form slides in the axial direction over the at least one second ratchet thread tooth form; and
b) rotating the ratchet ring with respect to the second body member so that the first and second ratchet thread tooth forms threadedly mate, thereby causing the second body member to move along the axial direction with respect to the first body member while the first body member remains stationary in the axial direction relative to the ratchet ring.

11. The method of claim 10, further comprising:
c) implanting the intervertebral implant between a first and a second vertebrae prior to steps (a) and (b).

12. The method of claim 10, further comprising:
c) applying a rotational force to the ratchet ring using a tool in step (b) so that the second body member moves axially with respect to the first body member; and
d) inserting bone chips through a window and into a cavity formed in the first body member of the implant to promote bone growth and fusion of the first and second vertebrae.

13. The method of claim 10 wherein the first ratchet thread tooth form comprises a series of teeth and the second ratchet thread tooth form comprises a series of teeth and wherein each of the teeth of the second ratchet thread tooth form can interdigitate with a corresponding tooth of the first ratchet thread tooth form when the two forms are fully engaged.

\* \* \* \* \*